United States Patent [19]

Nusbickel, Jr. et al.

[11] 4,375,167

[45] Mar. 1, 1983

[54] ULTRASONIC TRANSDUCER SUSPENSION SYSTEM FOR ON-LINE HIGH SPEED ULTRASONIC INSPECTION OF FLAT ROLLED PRODUCTS

[75] Inventors: Edward M. Nusbickel, Jr., Allentown; William L. Hutchinson, Quakertown; James E. Albert, Bethlehem, all of Pa.

[73] Assignee: Bethlehem Steel Corporation, Bethlehem, Pa.

[21] Appl. No.: 264,390

[22] Filed: May 18, 1981

[51] Int. Cl.³ .................. G01N 29/00; G01N 24/00
[52] U.S. Cl. .......................... 73/644; 73/628
[58] Field of Search .................. 73/644, 628; 29/121.6

[56] References Cited

U.S. PATENT DOCUMENTS

| 73,467 | 1/1868 | Seely | 29/121.6 |
|---|---|---|---|
| 1,828,510 | 10/1931 | Sammon | 29/121.6 X |
| 2,021,913 | 11/1935 | Fallon | 29/121.6 X |
| 2,524,208 | 10/1950 | Piper | 73/600 |
| 2,651,398 | 9/1953 | McGraw | 29/121.6 X |
| 2,875,607 | 3/1959 | Boxcer et al. | 73/628 X |
| 3,224,254 | 12/1965 | Loving | 73/644 |
| 3,534,591 | 10/1970 | Phelan | 73/634 |
| 3,616,684 | 5/1971 | Nusbickel, Jr. | 73/635 |
| 3,625,051 | 2/1971 | Uozumi | 73/639 |
| 3,662,590 | 5/1972 | Shiraiwa et al. | 73/644 |
| 3,678,735 | 4/1972 | Boulanger et al. | 73/640 |
| 3,777,554 | 12/1973 | Papay et al. | 73/644 X |
| 3,850,027 | 11/1974 | Nakanishi et al. | 73/600 |
| 3,910,104 | 7/1975 | Davies | 73/641 |
| 3,979,946 | 9/1976 | Cipywnyk | 73/635 |
| 4,041,773 | 8/1977 | Hauldren et al. | 73/638 |
| 4,047,274 | 9/1977 | Lehmann | 29/121.6 X |
| 4,070,905 | 6/1978 | Kossoff | 73/641 |

Primary Examiner—Edward R. Kazenske
Assistant Examiner—David V. Carlson
Attorney, Agent, or Firm—Joseph J. O'Keefe; Michael J. Delaney

[57] ABSTRACT

Apparatus and method for acoustically inspecting hot flat plates while on-line by utilizing an array or arrays of transducers continually spaced a set distance from the bottom of the plates by serrated rollers spring mounted with the array of transducers in a container with overflowing liquid wetting the passing plate to acoustically couple the transducers to the plate and a spray of sufficient force to temporarily cool the hot plate and dispel steam and vapor formed, the spray being in a direction opposite the direction of travel of the hot plate; and support of the unit on a track mounted carriage, with the liquid reused through a reservoir connected system. It is critical that the spray be at an angle of 27° or less to the horizontal and that the spray have sufficient force to have an apparent liquid velocity of at least 44 feet per second, adding the speed of the water and the hot plate together. Also includes associated electronic instrumentation and a rotary pulser with spring biased hinged mounted serrated roller having a cam activated limit switch for enabling the electronic instrumentation and a sprocket and chain connection from the serrated roller to a rotary pulse generator for detecting the position of the plates.

2 Claims, 8 Drawing Figures

ULTRASONIC TRANSDUCER SUSPENSION SYSTEM FOR ON-LINE HIGH SPEED ULTRASONIC INSPECTION OF FLAT ROLLED PRODUCTS

BACKGROUND OF THE INVENTION

The present invention relates to apparatus for rapid inspection of flat-rolled products while on-line at relatively high temperature with an accuracy, ease, and economy heretofore unknown in the industry utilizing ultrasonic detection of internal defects in flat-rolled products through streams of liquid applied to the flat-rolled products and synchronization of the flat products on the mill line with the automatic electronic instrumentation of the apparatus.

Available apparatus of the type of the present invention have one or more of the following disadvantages such as a much higher initial cost or maintenance cost, less inspection coverage, causing an obstruction of the passline, not being capable of reliable inspection at temperatures above 150° C. and not being able to follow contour variations. Designs with one or more of these disadvantages are found in closely related patents U.S. Pat. No. 3,625,051; Belgium Pat. No. 744,628; and U.S. Pat. No. 3,979,946 referring to ultrasonic measuring and inspecting systems.

Also the synchronizing of product motion for operation of the automatic controls as attempted in prior art devices now in use are designed with these devices mounted above the mill line and therefore present an obstruction along the line which prevents a crane from placing or removing anything in the area of the device.

SUMMARY OF THE INVENTION

It is an object of the present invention to eliminate all the disadvantages of the prior art devices within a rugged design.

Advantages of the present invention include the use of less water due to a circulation system, unobstructed pass-line, more tolerance to waviness in the flat-rolled product, better overall inspection resolution, inspection permitted at higher temperatures, and relative simplicity of construction, installation, and maintenance.

It is a further object of the present invention to locate the inspection device below the pass-line in order to maintain an unobstructed pass-line.

It is still a further object of the present invention to incorporate an immersion inspection technique in the invention to obtain better inspection resolution.

It is another object of the present invention to have a device which senses a flat product as it approaches a fixed location on a production line, and synchronizes the forward and backward movement of the product as the product passes over a fixed location.

Basically the present invention relates to a carriage for mechanically supporting and positioning an array of ultrasonic transducers used to ultrasonically detect internal defects in flat-rolled products, such as steel plates, and a delivery and storage system for providing a liquid such as water, that is used to cool the surface of warm (up to about 700° F.) flat-rolled products and also to provide a means for coupling ultrasound to and from the piece being inspected.

It is also an object of the present invention to install it on a mill line with suitable transducers and electronic instrumentation to provide a means for rapid one hundred percent ultrasonic inspection of both cool and warm (in the vicinity of 700° F.) flat-rolled products on-line during the production process.

A still further object of the present invention is to maintain vertical, horizontal, and axial adjustment of the transducer array.

In general the present invention comprises:

means for coupling ultrasonic energy to and from the tested piece and the transducer by means of both low pressure, high volume and at the same time velocity, low volume liquid flow;

means for supporting the transducer array and coupling assembly beneath a mill line on a suspension system that is independent from the main supporting assembly;

serrated roller means of contact with the inspected piece that allows a uniform or constant position of the transducer array relative to the test piece surface; and means for collecting ultrasonic coupling and cooling fluid, filtering it, storing it and recirculating it to the transducer through both low and high pressure lines.

BRIEF DESCRIPTION OF THE DRAWINGS

The above and other objects and advantages of the invention will become apparent upon full consideration of the following detailed description and accompanying drawings in which.

DESCRIPTION OF THE PREFERRED EMBODIMENTS

Figure 1:
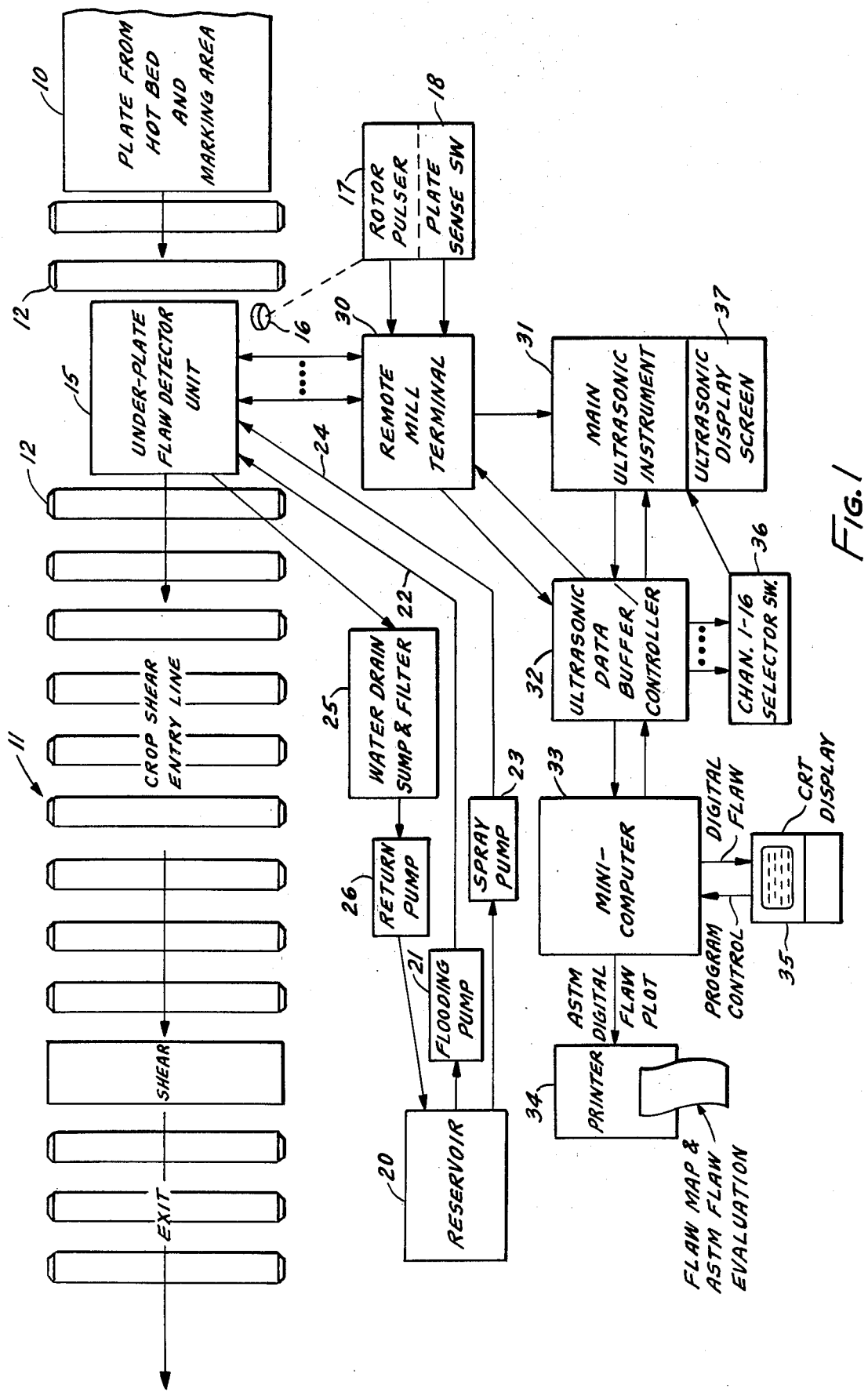
FIG. 1 is a block diagram of the overall system of the present invention.

Referring first to FIG. 1 there is shown an overall block diagram of the apparatus of the present invention for on-line ultrasonic inspection of steel plates.

A steel plate 10 which may still be at a high temperature is moved over roll table 11 from a hot bed and marking area. In between a pair of rollers 12 there is located an under-plate flaw detector unit 15 which performs inspections utilizing ultrasonics on plates 10 as they pass over the rollers and unit 15. Also located in the passline is a serrated wheel 16 driven by plate 10 as it passes over it. Wheel 16 is mechanically connected to rotor pulser 17 which is used to determine the position and change of position of plate 10 on the pass-line. The ultrasonic inspection of flaw detector unit 15 utilizes water from reservoir 20 which is delivered both through flooding pump 21 in a low pressure, high volume stream through hose line 22 to flaw detector unit 15 and through spray pump 23 in a high pressure, low volume stream through hose line 24 to unit 15. After use the water from unit 15 passes through water drain sump and filter 25 through return pump 26 to reservoir 20 for further use in the system.

A remote mill terminal 30 connects to flaw detector 15 so as to operate unit 15 with proper signals and receiving information as to any flaws in plates 10 therefrom. At the same time plate travel is synchronized with the electronic instrumentation through information received from rotor pulser 17 which is mechanically connected to wheel 16 which is spring loaded to maintain frictional contact with the bottom of plate 10. Combined with information from plate sensor switch 18 the pressure of a plate 10 as well as forward and backward plate motion are sensed. Remote mill terminal 30 activates main ultrasonic instrument 31 which through ultrasonic data buffer/controller 32 supplies ultrasonic power to flaw detector unit 15 and supplies the information to minicomputer 33 and printer 34 and CRT display 35 to indicate flaws. Channel selector switch 36 chooses the ultrasonic transducer/channel/s whose signals will be displayed on the ultrasonic display screen 37, as plate 10 moves over flaw detector unit 15.

Figure 2:
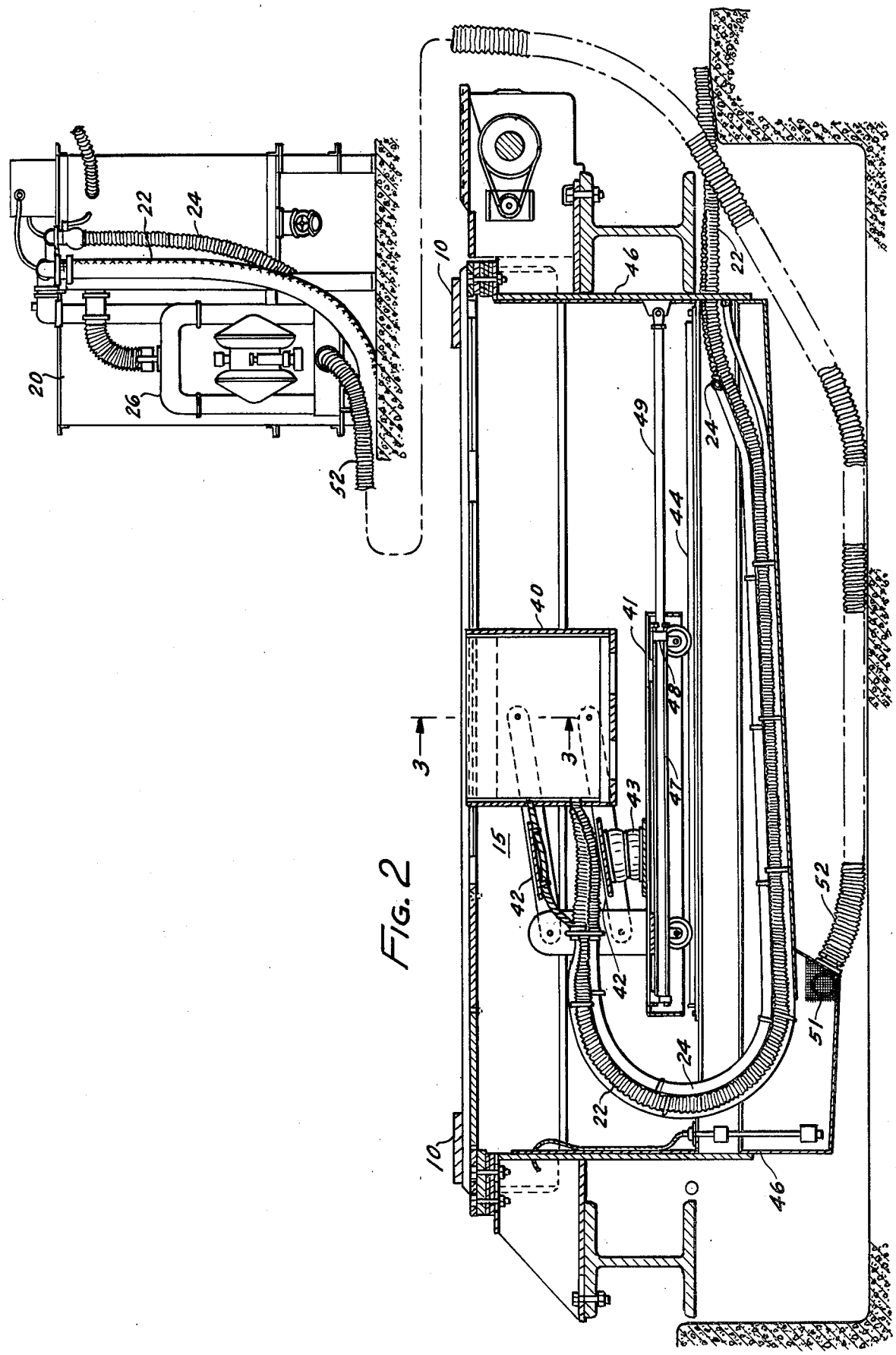
FIG. 2 is a partially sectioned transverse elevation of the on-line portion of the present invention and a view of connecting apparatus.

Flaw detector unit 15 is shown in FIG. 2 in its mounting and with its hose connections to reservoir 20. Further details of the internal structure of unit 15 is shown in elevation and plan views in FIGS. 3 and 4 respectively.

Refering to FIG. 2 there is shown a steel container 40 into which water runs and which contains an ultrasonic transducer fixture. Container 40 with a transducer array therein is mounted on a wheeled carriage 41. Container 40 is cantilevered on carriage 41 by a set of hinged parallel bars 42. A bellows type air bag 43 supports the cantilevered container 40 and permits the raising and lowering of it by remote pneumatic control. If desired, the air bag remote control may be connected to a sensing device located upstream from the transducer container 40 so that it can automatically retract air bag 43 if a severely bent plate is sensed at the upstream sensing device. Wheeled carriage 41 rests on tracks 44 supported within a water collection trough and sump 46 (or 25 of FIG. 1). An air cylinder 47 on carriage 41 has its piston 48 connected to the side of trough 46 through connecting rod 49. Thus it is possible to control the position of carriage 41 for transverse movement across mill line or pass-line by remote pneumatic control. Flexible hoses 22 and 24 respectively carry low pressure, high volume and high pressure, low volume liquid from reservoir 20 to container 40. Liquid overflowing transducer container 40 is collected in sump trough 46 and returned to the reservoir 20 via filter 51 and flexible hose 52. The water collection, filtering and storage reservoir reduces the amount of water usage and permits economical use of various additions to the water such as anti-freeze and/or wetting agents by reducing the need for continual make-up as is the case in existing systems that continually drain away coupling water.

Figure 3:
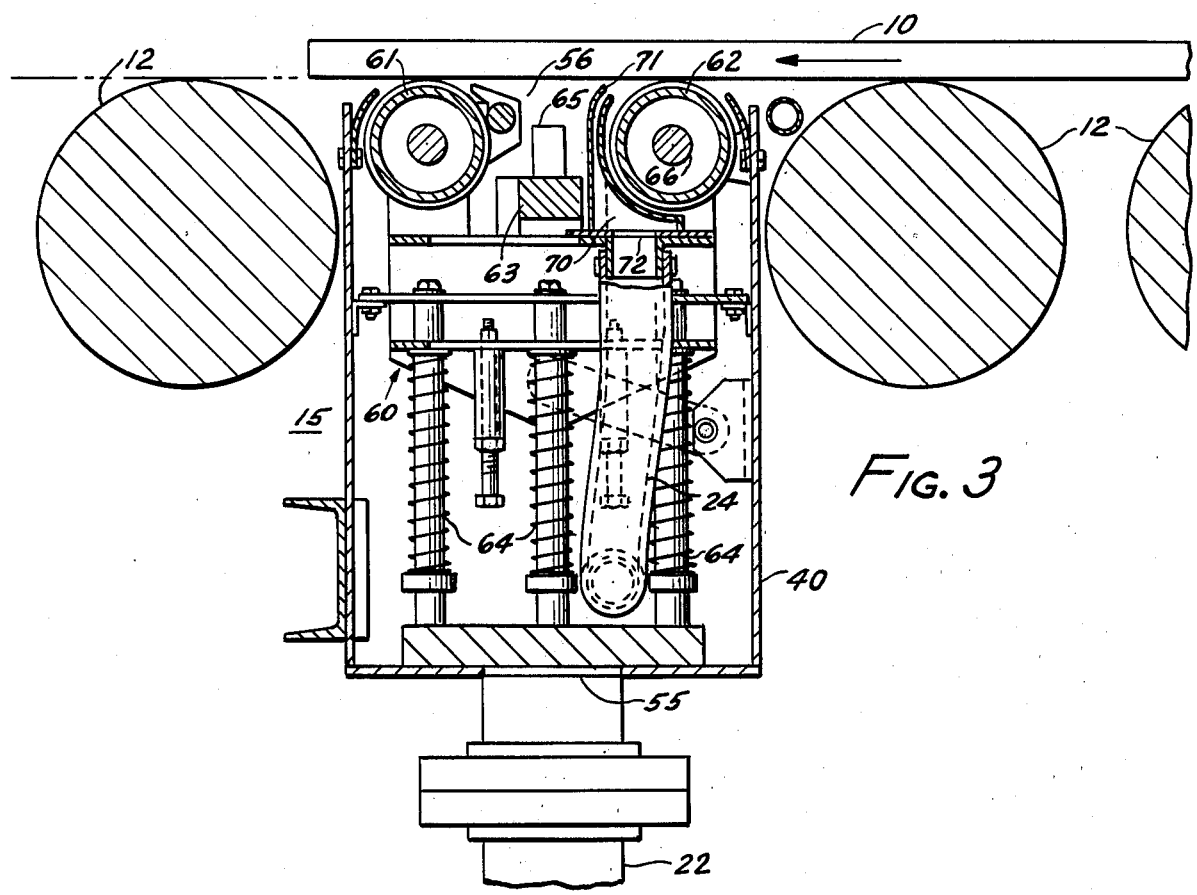
FIG. 3 is a partially sectioned enlarged view of the under-plate ultrasonic flow detector unit along line 3—3 of FIG. 2.
Figure 4:
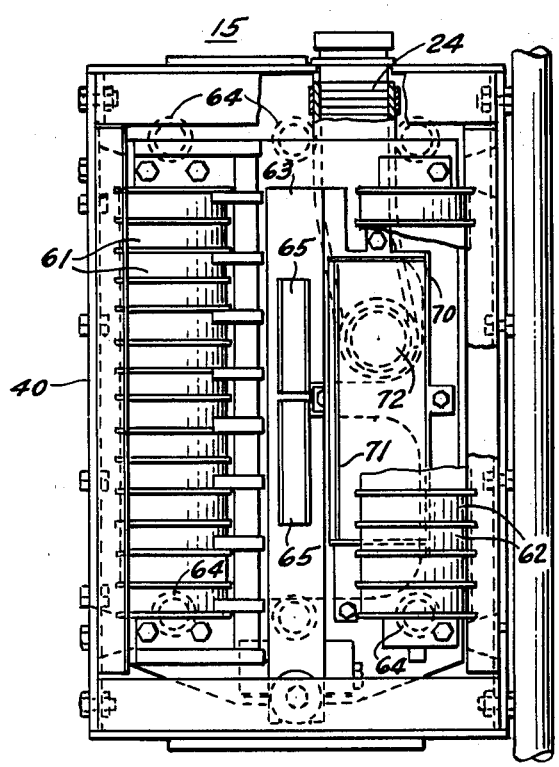
FIG. 4 is a plan view of the unit of FIG. 3.

Container 40 as shown in more detail in FIGS. 3 and 4 has a water flow into the container through flexible hose 22 at inlet 55 at a rate between 175 and 200 gpm. As the water fills portion 56 of container 40, the container walls act as a weir and hydraulic equations for water flowing over a weir apply. A plate 10 moving over the top of container 40 is wetted on its lower surface by the water as it swells up over the container walls. Mounted in container 40 is a spring loaded assembly 60. On assembly 60 are grooved or serrated rollers or cylinders 61 and 62 mounted so that their axes of rotation are parallel to the plane of a plate 10 and perpendicular to the direction of travel of that plate 10. Between rollers or rolls 61 and 62 is a transducer mounting bar 63. Container 40 is generally mounted between pass-line rolls 12 on a plate mill so that the upper rims of serrated rolls 61 and 62 rise a distance above the pass-line rolls 12 equal to the expected maximum waviness of the plate 10 to be inspected. In the embodiment of a plate mill illustrated serrated rolls 61 and 62 may be placed so as not to exceed one inch above the pass-line. As plates 10 move down the production line, their bottom surface contacts serrated rolls 61 and 62 which causes assembly 60 in container 40 to be compressed against springs 64. This spring pressure causes serrated rolls 61 and 62 to follow the bottom surface contour of plate 10 and thus maintain uniform positioning of transducers 65 with respect to the lower plate surface as plate 10 moves over assembly 60. The independently suspended or isolated transducer array shown makes it possible for the array of transducers 65 to follow wavy surfaces on plates 10 and thereby maintain a constant distance between transducers 65 and plate 10. Also the ultrasonic beam can be maintained relatively normal to the inspected piece surface regardless of the up and down motion of the piece due to waviness of plate 10. If it is desired and as shown in the present embodiment, transducer mounting bar 63 can have means for adjustment for transverse alignment of transducers 65 and also serrated roll 62 can be supported by an eccentric shaft 66 that permits longitudinal adjustment of transducers 65. Flowing water contacting the bottom of plate 10 provides ultrasonic coupling with transducers 65 in a manner similar to a standard immersion test. The low pressure, high volume liquid supply makes it possible to position the ultrasonic transducers away from the inspected plate surface while ultrasonic coupling is achieved through a liquid column. Thus, the risk of transducer damage from rough or projecting surfaces of the inspected plate is greatly reduced. The type of inspection performed is similar in principle to immersion type inspection which is recognized by those familiar with ultrasonic inspection as producing more consistant results and higher resolution than most other common methods of ultrasonic inspection.

Also mounted on spring loaded assembly 60 is a separate fluid chamber 70 with slotted orifice 71 that directs water at an angle of 27° or less relative to the bottom surface of plate 10 in a direction opposite to plate travel. A separate inlet 72 to chamber 70 is connected to flexible hose 24 which extends into container 40 and through which liquid at higher pressure than the liquid in portion 56 of container 40 enters chamber 70 and is directed through orifice 71 onto the bottom surface of plate 10 with high enough velocity to wash away steam and vapor and to temporarily cool the surface of plate 10 which may be at a temperature of about 700° F. Ultrasonic coupling into a warm plate is thereby affected. Water pressure in slotted chamber 70 is such that the velocity of the water and the opposing plate velocity combine to produce an apparent liquid velocity of at least 44 feet per second impinging on the plate surface. For a warm plate, coupling fluid temperature should be as low as possible to inhibit rapid steam generation. The high velocity, low volume liquid flow permits inspection at higher plate temperatures because a flow is produced which when directed tangentially onto the plate surface serves to temporarily cool the surface and wash generated steam away from the ultrasonically inspected area.

Figure 5:
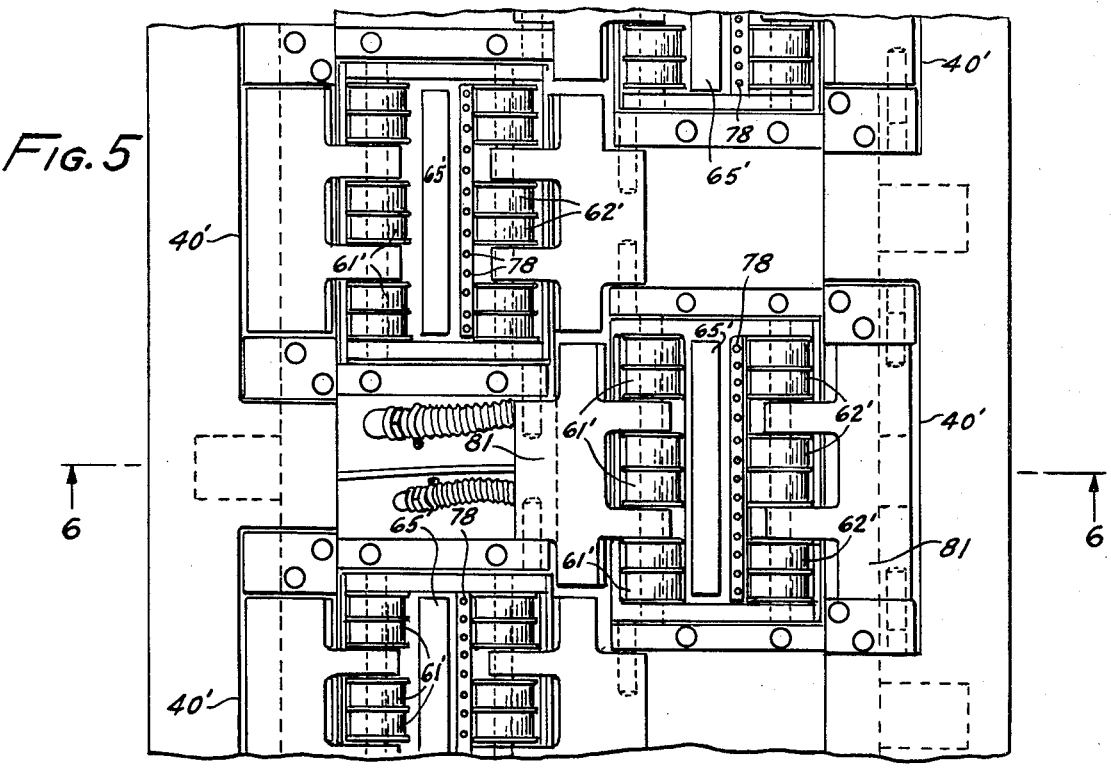
FIG. 5 is a plan view of units similar to those of FIG. 3 but located for full width inspection.
Figure 6:
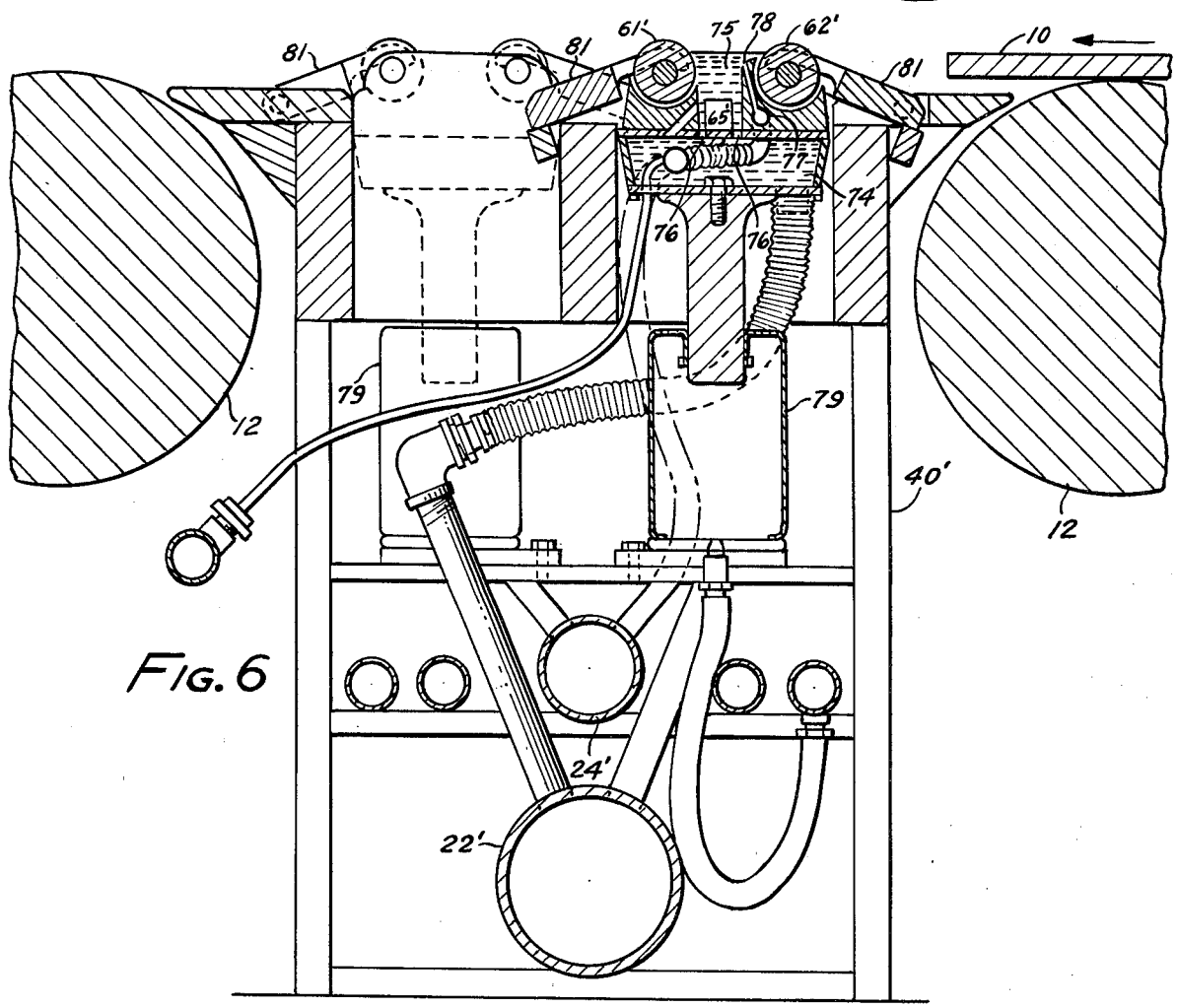
FIG. 6 is an elevation of the embodiment of FIG. 5 along line 6—6 of FIG. 5.

The embodiment described above requires transverse adjustment of the transducer array and possibly several passes of a plate 10 in order to inspect the full width. FIGS. 5 and 6 disclose another embodiment allowing ultrasonic inspection of the full width during a single pass. A series of containers 40' with serrated rolls 61', and 62' and arrays of transducers 65' are installed across a mill line between pass rolls 12. Containers 40' are positioned in staggered fashion so that the inspection path from an array of transducers 65' in one container 40' is adjacent to the inspection path of an array of transducers 65' in another container 40' with no intervening uninspected space. Low and high pressure liquid is supplied to containers 40' through manifolds 22' and 24' respectively located under the transducer arrays. Connecting pipes and flexible hoses connect low pressure manifold 22' to chamber 74 from which flooding water passes through openings 76 to portion 75 from which the water wets the bottom surface of plate 10 while it is overflowing. Other connecting pipes and flexible hoses connect spray manifold 24' to chamber 77 from which spray is ejected from orifice 78 against plate 10. Each array of transducers 65' with serrated rolls 61' and 62' and flooding and spraying structure is supported by air bags 79 that provide the constant contact of rolls 61' and 62' on the bottom surface of plate 10. Ramps 81 leading to and from serrated rolls 61' and 62' serve to reduce mechanical shock to transducer arrays 65' as a plate 10 approaches the inspection fixture. The combination of ramps 81 with the staggered transducer arrays 65' minimize the possibility that bent plates can damage transducer arrays 65'. The entire assembly can be fixed on a framework that can be installed as one piece and supported on an existing pass-line framework. Liquid supply pumps, reservoir and filters may be located on the side of the pass-line near the on-line assembly.

Figure 7:
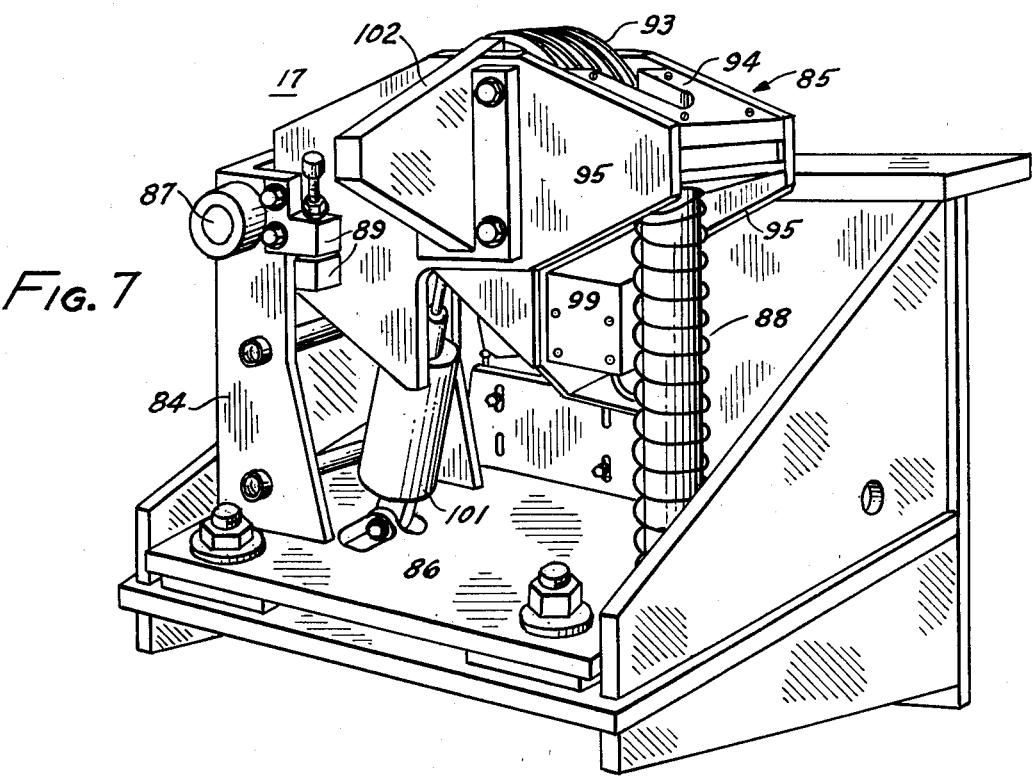
FIG. 7 is a perspective view of the rotor pulser and plate sensor unit from one side of the unit.
Figure 8:
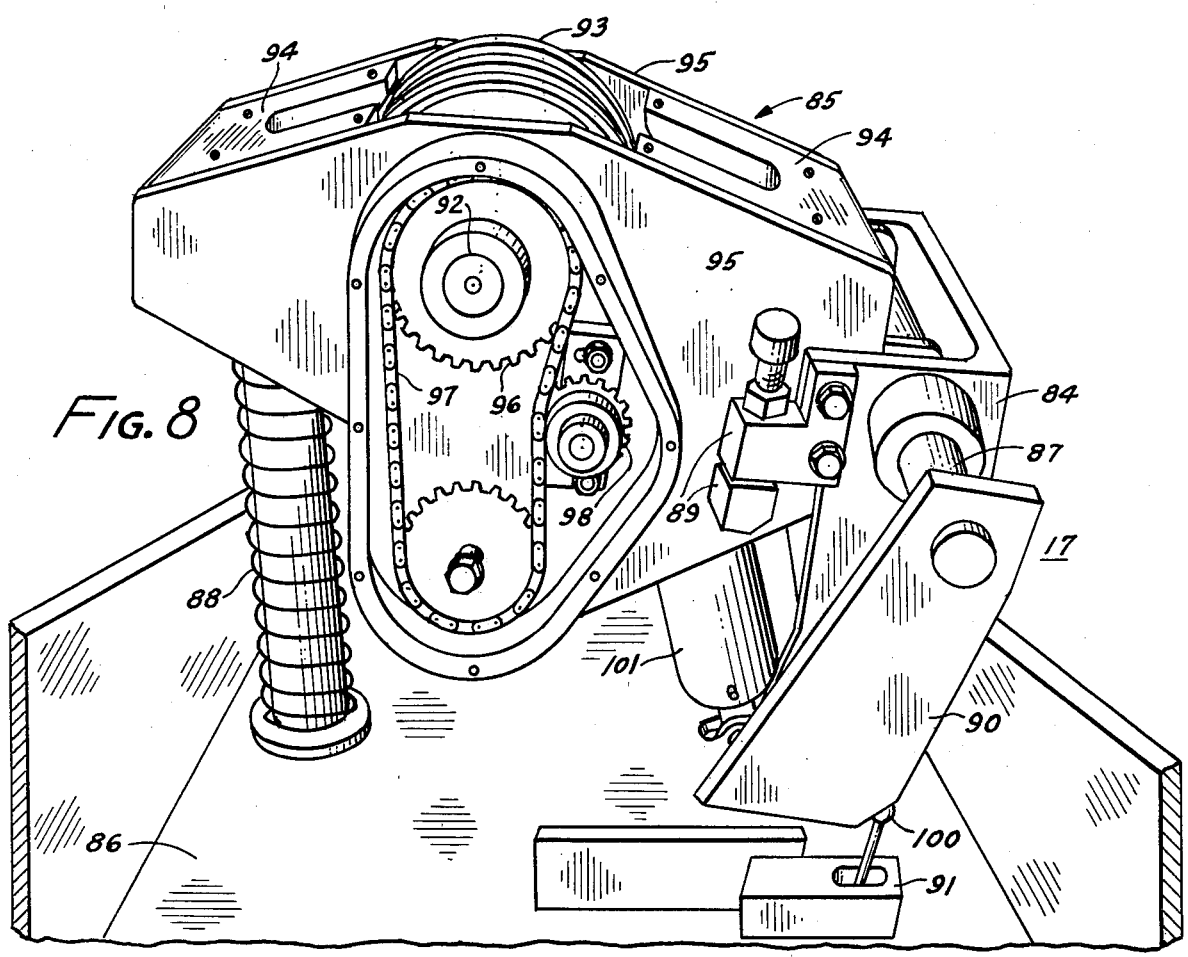
FIG. 8 is a perspective view of the unit in FIG. 7 from the opposite side.

FIGS. 7 and 8 are detail views of rotor pulser 17 showing its mechanical construction. The roto-pulse assembly 85 is mounted on a pair of vertical plates 84 welded to a base plate 86 with a shaft 87 rigidly attached to one end of assembly 85 and passing through bushings on vertical plates 84. A spring mechanism 88 spaced horizontally on the other end of assembly 85 from shaft 87, and stop mechanism 89, permit assembly 85 to be fixed at one point relative to vertical plates 84 and base plate 86 yet able to travel through a limited arc rotated on shaft 87 when the pressure of spring mechanism 88 is overcome. Rigidly connected to an extension of shaft 87 is a cam 90 that activates a limit switch 91 (such as plate sensor switch 18 as in FIG. 1), mounted to base plate 86, when the roto-pulse assembly 85 moves down slightly on spring mechanism 88 from its fixed bias point in a movement with shaft 87. On assembly 85 another shaft 92 passes through bushings on the hinged assembly 85 and is rigidly attached to a serrated roller 93. The roller 93 (serrated wheel 16 of FIG. 1) is located in assembly 85 such that the top sections 94 and sidewalls 95 of assembly 85 protect roller 93. A sprocket 96 and chain 97 connect serrated roller 93 to sprocket 98 which is connected to a commercially available rotary pulse generator 99 such as is manufactured by Gould, Incorporated, Control Systems Division of Wilmington, Maine. Rotary pulse generator 99 is also mounted on roto-pulse assembly 85 on the opposite side of a sidewall 95 from sprocket 98. Electrical cable connects from rotary pulse generator 99 to remote synchronizing and timing circuitry.

The entire roto-pulse assembly 85 is mounted between rolls 12 on a production line such that the circumference of serrated roller 93 rises above the pass-line at a distance equal to the expected maximum waviness of the product plate 10 to be tracked. The top sections 94 of roto-pulse assembly 85 then act as ramps in front of and behind serrated roller 93 and serve to cushion the impact as the plate contacts assembly 85. As plate 10 approaches assembly 85 serrated roller 93 is depressed and cam 90 depresses the follower 100 on switch 91 which is used to enable the synchronizing instrumentation. As plate 10 moves over assembly 85 serrated roller 93 follows the lower surface of plate 10. Friction causes roller 93 to rotate and in turn causes rotary pulse generator 99 to rotate and produce a series of electrical pulses that are synchronized with plate 10 movement. Rotor pulser unit 17 feeds the electrical pulses to remote mill terminal 30. The serrations on roller 93 reduce the possibility that small particles clinging to the surface of plate 10 will cause assembly 85 to skip or miss pulses. An air cylinder 101 under roto-pulse assembly 85 permits the assembly to be retracted beneath the pass-line when not in use or when conditions on the line could damage it if it were left engaged. A beveled fillet 102 along the side of assembly 85 permits plate 10 to be shifted sideways on and off assembly 85 with no damage.

By use of roto-pulse assembly 85 with rotary pulse generator 99 and ultrasonic flaw detector unit 15 with its associated parts, flaws are detected in plates 10 and accurate recording of the location of these flaws can be made.

It will be obvious to those skilled in the art that various changes may be made without departing from the scope of the invention and the invention is not to be considered limited to what is shown in the drawings and described in the specification.

We claim:
1. Ultrasonic apparatus for testing a hot flat workpiece located below and along the path of the workpiece comprising
   ultrasonic transducer means having at least one multiplexed array of ultrasonic transducers, each transducer capable of transmitting an ultrasonic beam into the workpiece and receiving a reflected beam signal,
   spraying means directing a spray against the bottom of the workpiece in a direction opposite the direction of travel of the workpiece at an angle of approximately 27° or less to the bottom of the workpiece to cool the hot workpiece and remove steam vapor formed at the workpiece,
   said spraying means sprayed at an apparent liquid velocity of at least 44 feet per second by combining the velocity of the liquid and the opposing velocity of the workpiece moving along its path,
   guiding means to allow said ultrasonic transducer means to follow the contours of the surface of the workpiece,
   a container holding said transducer means, spraying means and guide means,
   a flooding means in said container and overflowing said container for acoustical coupling; and,
   all said transducer means, spraying means, container and flooding means, and guiding means completely located beneath the path of the workpiece.

2. A method of testing a hot flat workpiece for flaws therein comprising the steps of moving the workpiece along a path or pass-line, spraying a stream of liquid from and against the bottom of the hot workpiece at an angle of approximately 27° or less relative to the bottom of the workpiece and in a direction opposite to the direction of movement of the workpiece and at a velocity of at least 44 feet per second with enough pressure to disperse steam formed from the contact of cooling fluid with the hot workpiece, acoustically coupling to the bottom of the workpiece through a liquid medium by overflowing a container having ultrasonic transducers therein, to a height to wet the adjacent bottom surface of the workpiece, transmitting and receiving ultrasonic signals through said liquid medium and from and to a location beneath the path of the workpiece, recording and interpreting for test results said received ultrasonic signals.

* * * * *